United States Patent [19]

Shibatani et al.

[11] 4,300,002

[45] Nov. 10, 1981

[54] PROCESS FOR PRODUCING POLYCYCLIC DIOLS

[75] Inventors: Haruo Shibatani; Yuji Ogomori; Takashi Kameda, all of Ami; Yoshio Yanagi, Yokkaichi, all of Japan

[73] Assignee: Mitsubishi Petrochemical Co., Ltd., Tokyo, Japan

[21] Appl. No.: 125,877

[22] Filed: Feb. 29, 1980

[30] Foreign Application Priority Data

Mar. 5, 1979 [JP] Japan ................................ 54/24545

[51] Int. Cl.³ .............................................. C07C 35/22
[52] U.S. Cl. ..................................... 568/817; 568/820
[58] Field of Search ................ 568/817, 820, 444, 909

[56] References Cited

U.S. PATENT DOCUMENTS

| | | | |
|---|---|---|---|
| 2,850,536 | 9/1958 | Buchner et al. ..................... | 568/817 |
| 3,239,569 | 3/1966 | Slaugh et al. ....................... | 568/444 |
| 3,311,598 | 3/1967 | Mertzweiller et al. .............. | 568/817 |
| 3,488,296 | 1/1970 | Senn et al. .......................... | 568/444 |

Primary Examiner—Werren B. Lone
Attorney, Agent, or Firm—Oblon, Fisher, Spivak, McClelland & Maier

[57] ABSTRACT

A polycyclic diol is produced by a hydroformylation of a polycyclic bridged ring olefinic compound having another double bond, formyl or methylol group, in the presence of a cobalt compound and a phosphine as a catalyst in the presence of a saturated hydrocarbon or aromatic hydrocarbon.

Polycyclic diols such as tricyclodecanedimethylol are useful for hardeners for non-solvent type lacquers polyurethanes having heat resistant and chemical resistance or epoxy resins.

12 Claims, No Drawings

PROCESS FOR PRODUCING POLYCYCLIC DIOLS

BACKGROUND OF THE INVENTION

1. Field of the Invention

The present invention relates to a process for producing a polycylic diol by using carbon monoxide, hydrogen and a polycyclic bridged ring olefinic compound having another double bond, formyl or methylol group (at the other side of bridgehead carbon).

2. Description of the Prior Arts

Polycyclic diols are useful as intermediates for nonsolvent type lacquers having excellent hardness, polyurethanes having heat resistance and chemical resistance and hardeners for epoxy resins etc.

The typical polycylic diol is tricyclodecanedimethylol and accordingly, the process for producing tricyclodecanedimethylol by a hydroformylation of dicyclopentadiene will be mainly described.

The oxo reaction of dicyclopentadiene is carried out in the presence of a cobalt compound, a diluent, a polymerization inhibitor and a stabilizer at 120° to 150° C. under a pressure of 180 kg/cm$^2$ to obtain tricyclodecanedimethylal and then, the tricyclodecanedimethylal is hydrogenated in the presence of a nickel catalyst to obtain tricyclodecanedimethylol in G.B. Pat. No. 750,144.

The oxo reaction of dicyclopentadiene is carried out in the presence of a rhodium compound and a diluent at 125° to 140° C. under the pressure of 200 to 250 kg/cm$^2$ to obtain tricyclodecanedimethylal and then, the hydrogenation of the product is carried out in the presence of the same catalyst than 180° C. to obtain tricyclodecanedimethylol in G.B. Pat. No. 1,170,226.

Thus, in these processes, two steps for the reactions are required and high pressure should be applied. In the latter process using the rhodium catalyst, the catalyst is disadvantageously expensive. Both processes are not satisfactory.

On the other hand, it has been known to carry out a hydroformylation of an olefin compound in the presence of a catalyst of a cobalt compound and a phosphine.

In accordance with this process, the catalyst is economical and the reaction pressure is lower and the alcohol is obtained by one step reaction. This process is employed as an industrial processes for producing n-butanol or a higher alcohol as a detergent source. It has not found to apply this process to dicyclopentadiene.

The hydroformylation using a cobalt compound and a phosphine as catalyst is usually carried out at a temperature of higher than 160° C. especially about 200° C. whereby the alcohol can be obtained in one reaction step. On the other hand, dicyclopentadiene is usually decomposed into cyclopentadiene by a reverse Diels Alder reaction at higher than 150° C. Therefore, in the conventional hydroformylation at such high temperature, an yield of tricyclodecanedimethylol is lower and an inactivation of the catalyst caused by cyclopentadiene is found as described in Chem. Prum. 19, 359(1969) C.A. 72, 11777. This phenomenon may be considered in the conventional processes since it is carried out at lower than 160° C.

In order to produce tricyclodecanedimethylol by the hydroformylation using a cobalt compound and a phosphine as a catalyst, it may be necessary to find a special method for performing predominant hydroformylation under preventing the decomposition of dicyclopentadiene. It has been expected to attain a remarkably effective process for producing tricyclodecanedimethylol if said ideal conditions can be found.

SUMMARY OF THE INVENTION

It is an object of the present invention to produce a polycyclic diol at high yield by a hydroformylation of a polycyclic bridged ring olefinic compound having another double bond, formyl or methylol group (at the other side of bridgehead carbon) at high temperature in an economical one step reaction.

It is another object of the present invention to produce a polycyclic diol at high yield in the presence of a cobalt carbonylphosphine complex as a catalyst and to reuse the catalyst components by an advantageous manner.

The foregoing and other objects of the present invention have been attained by producing a polycyclic diol by a hydroformylation of a polycyclic bridged ring olefinic compound having another double bond, formyl or methylol group (at the other side of bridgehead carbon) in the presence of a cobalt compound and a phosphine as a catalyst in the presence of a saturated hydrocarbon or aromatic hydrocarbon solvent and the reaction mixture is cooled to result a phase separation into a solvent phase containing the catalyst and a polycyclic diol phase and the solvent phase is recycled into the reaction system.

DETAILED DESCRIPTION OF THE PREFERRED EMBODIMENTS

The process of the present invention is remarkably advantageous because the hydroformylation of the polycyclic bridged ring olefinic compound having another double bond, formyl or methylol group can be predominantly performed at a high temperature for causing a decomposition of said starting material.

In the industrial process using a cobalt compound and a phosphine as the catalyst, it is advantageous to separate the catalyst from the product and to reuse the separated catalyst in the hydroformylation.

Certain processes have been proposed to separate the catalyst and the solvent from tricyclodecanedimethylal produced by the hydroformylation or from tricyclodecanedimethylol produced by the hydrogenation of said dimethylal.

The hydroformylation is carried out by using cobalt naphthenate as the catalyst and using hexane as the solvent and the reaction mixture is cooled to separate it into a solvent phase and a tricyclodecanedimethylal phase and the solvent phase is recycled into the reactor and the cobalt component is separated by a thermal decomposition from the tricyclodecanedimethylal phase in G.B. Pat. No. 728,913.

The hydroformylation is carried out by using cobalt sulfate as the catalyst and using heptane as the solvent and the reaction mixture is cooled to separate it into three phases of a heptane phase, an aqueous phase and a tricyclodecanedimethylal phase. The cobalt component is allotted to about 10%, about 53% and about 37% respectively in said phases. A new catalyst for hydrogenation is added to the tricyclodecanedimethylal phase and the hydrogenation is carried out at an elevated temperature to convert it into tricyclodecanedimethylol and also to remove the cobalt component in G.B. Pat. No. 765,742.

When the cobalt-magnesium oxide-thorium oxide-diatomaceous earth is used as the catalyst and heptane is used as the solvent, the reaction mixture is separated into a heptane phase and a tricyclodecanedimethylal phase. The catalyst is suspended in the tricyclodecanedimethylal phase and is removed by the same manner.

Two step reactions are carried out by using rhodium oxide as the catalyst and benzene as the solvent to obtain tricyclodecanedimethylol and the rhodium component is separated by a thermal decomposition in G.B. Pat. No. 1,170,226.

In these processes, the phase separation is carried out by selecting the solvent. Most of the catalyst is remained in the product phase and the catalyst is separated from the product by the thermal decomposition. In these processes, when a cobalt compound is used, the metallic cobalt is adhered on the wall of the reactor and accordingly, it is not advantageous for the recycling of the catalyst component. Moreover, these processes are not employed for the separation of the catalyst containing the phosphine.

On the other hand, in an industrial process of hydrofomylation using a phosphine with a cobalt compound or a rhodium compound, the reaction mixture is distilled to separate it into the product and a complex of the phosphine and the metal carbonyl since the metal carbonyl-phosphine complex is stable. However, tricyclodecanedimethylol has remarkably high boiling point (about 170° C./1 mmHg) and accordingly, the cobalt carbonyl-phosphine complex is not stable at the temperature for the distillation. This process is not also advantageous.

The inventors have further studied to dissolve these problems and have found the following fact.

When the hydroformylation is carried out by using a cobalt compound and a phosphine as the catalyst and using a hydrocarbon as the solvent, the solvent phase is separated from the product of tricyclodecanedimethylol by a phase separation caused by cooling the reaction mixture. Most of the cobalt component and the phosphine are included in the solvent phase and accordingly, the catalyst can be easily separated from the product.

In the conventional process for producing tricyclodecanedimethylal by using only a cobalt compound as the catalyst, the phase separation of the solvent phase and the product phase is carried out, most of the catalyst is included in the product phase and accordingly, the separation of the catalyst from the product could not be succeeded.

On the contrary, in the process for producing tricyclodecanedimethylol by using the cobalt compound and the phosphine as the catalyst most of the catalyst is included in the solvent phase whereby the separation of the catalyst from the product can be easily attained by the phase separation. This reason is considered as follows.

The product is different as tricyclodecanedimethylal is produced in the former whereas tricyclodecanedimethylol is produced in the latter and the catalyst is different as a cobalt carbonyl complex is used in the former whereas a cobalt carbonyl-phosphine complex is used in the latter and affinities of the product, the solvent and the catalyst are different.

It has not been expected that the distributions of the catalyst in the solvent phase and the product phase are opposite by said slight differences of the reaction conditions.

In the conventional process, only a saturated hydrocarbon is used as the solvent for the phase separation. In the process of the present invention, it has been found that an aromatic hydrocarbon can be also effectively used.

In accordance with the present invention, the hydroformylation of a polycyclic bridged ring olefinic compound having another double bond, formyl or methylol group (the starting material) is carried out in the presence of a cobalt compound and a phosphine as the catalyst and a saturated hydrocarbon and/or an aromatic hydrocarbon as the solvent and the resulting reaction mixture is cooled to separate it into a solvent phase containing the catalyst and a product phase and the solvent phase is recycled into the hydroformylation reaction system.

The present invention can be applied for the production of various polycyclic diols from the polycyclic bridged ring olefinic compound having another double bond, formyl or methylol group under the similar reaction condition. In order to simplify the description of the process of the present invention, the production of tricyclodecanedimethylol from dicyclopentadiene will be illustrated as the typical example. The starting material can be varied to obtain the corresponding product.

1. MATERIALS USED IN THE REACTION (1) Polycyclic bridged ring olefinic compound having another double bond, formyl or methylol group.

The polycyclic bridged ring olefinic compound having another double bond, formyl or methylol group (at the other side of bridgehead carbon) include the compounds having the formula

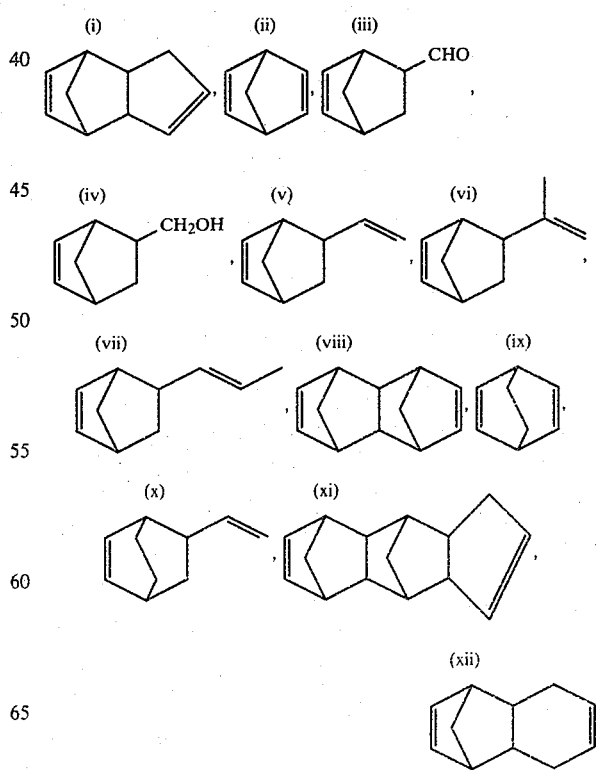

(i) tricyclo[5.2.1.0$^{2,6}$]deca-3,8-diene, (this is usually called as dicyclopentadiene),
(ii) bicyclo[2.2.1]hepta-2,5-diene,
(iii) bicyclo[2.2.1]hept-5-ene-2-carboxaldehyde,
(iv) bicyclo[2.2.1]hept-5-ene-2-methylol,
(v) 5-vinyl-bicyclo[2.2.1]hept-2-ene,
(vi) 5-isopropenyl-bicyclo[2.2.1]hept-2-ene,
(vii) 5-propenyl-bicyclo[2.2.1]hept-2-ene,
(viii) tetracyclo[6.2.1.1$^{3,6}$.0$^{2,7}$]dodeca-4,9-diene,
(xi) bicyclo[2.2.2]octa-2,5-diene,
(x) 5-vinyl bicyclo[2.2.2]oct-2-ene,
(xi) pentacyclo[9.2.1.1$^{3,9}$.0$^{2,10}$.0$^{4,8}$]pentadeca-5,12-diene,
(xii) tricyclo[6.2.1.0$^{2,7}$]undeca-4,9-diene.

The typical starting material is dicyclopentadiene and accordingly, the present invention will be described in detail on the process for producing tricyclodecanedimethylol from said starting material.

Products (polycyclic diols)

The following polycyclic diols are produced by using the polycyclic bridged ring olefinic compounds (i) to (xii). (The references are corresponding with the starting materials.)

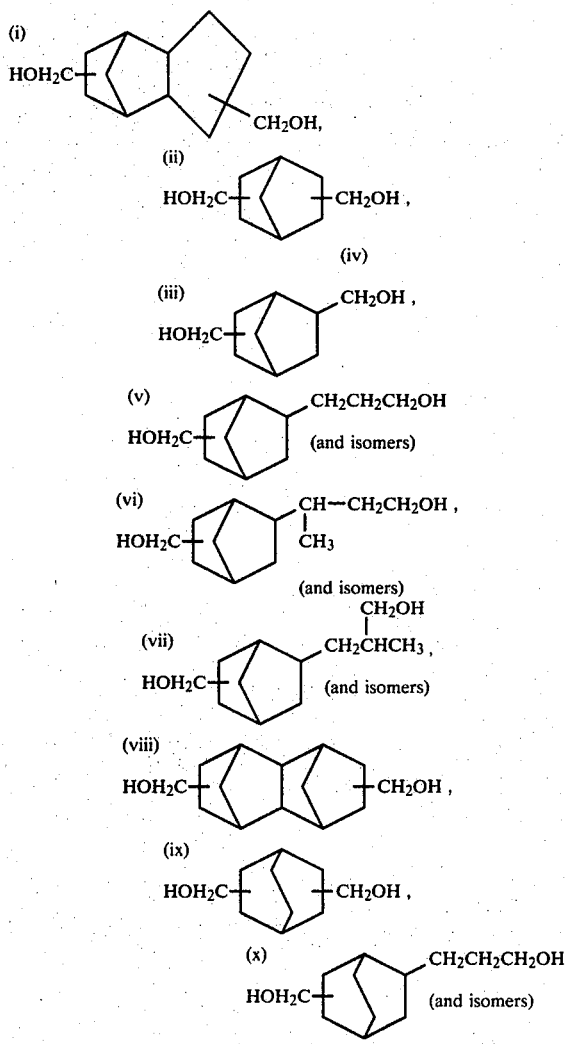

Dicyclopentadiene as the starting material can be produced by Diels Alder reaction of cyclopentadiene. The industrial product of cyclopentadiene obtained by the naphtha cracking as a C$_5$-fraction can be used.

(2) Synthesis gas

The synthesis gas contains CO and H$_2$ at a molar ratio of CO/H$_2$ of 5:95 to 95:5 preferably 2:1 to 1:2. It is possible to mix an inert gas such as nitrogen, argon, carbon dioxide and methane as far as it does not adversely affected to the reaction.

2. CATALYST (1) Cobalt compound

The cobalt compounds are preferably cobalt carbonyl complexes such as dicobalt octacarbonyl or hydro cobalt tetracarbonyl.

The precursors such as compounds which form carbonyl complexes in the reaction, such as metallic cobalt; cobalt oxide, cobalt halides, cobalt acetates, cobalt octanoates and cobalt naphthenates can be used.

(2) Phosphine

The phosphines having the formula

R$_3$P wherein R is the same or different and respectively represent hydrocarbon moiety, can be used. It is especially preferable to use the phosphines having saturated aliphatic group or alicyclic hydrocarbon group as the hydrocarbon moiety.

Suitable phosphines include tri-n-butylphosphine, tri-n-octylphosphine, tri-n-dodecylphosphine and tricyclohexylphosphine. Bicyclic heterocyclic phosphines such as 9-eicosyl-9-phosphabicyclo [4.2.1]nonane, 9-eicosyl-9-phosphabicyclo 3.3.1 nonane, 8-eicosyl8-phosphabicyclo[3.2.1]octane and 8-octadecyl-8-phosphabicyclo [3.2.1]octane, are also suitable. Polydentatephosphines such as 1,2-bisdiethylphosphinoethane, octamethylene-P,P'-bis(9-phosphabicyclo[4.2.1]nonane can be also used. A mixture thereof can be also used.

3. SOLVENT

The solvents used in the reaction can be saturated aliphatic hydrocarbons, alicyclic hydrocarbons, aromatic hydrocarbons and mixtures thereof.

It is preferably to use the solvent which have 6 or more carbon atoms and is liquid at the separation temperature.

Suitable solvents include n-hexane, n-octane, n-dodecane, n-tetradecane, cyclohexane, methylcyclohexane, decalin, "liquid paraffin" made of alkyl naphthenes, benzene, toluene, butylbenzene, dodecylbenzene and mixtures thereof.

It is possible to use a mixed solvent containing a compound having polar group with the hydrocarbon if it does not adversely affected.

4. CONDITIONS FOR REACTION

The conditions for reaction are selected as follows.

The reaction temperature is usually in a range of 100° to 250° C. preferably 150° to 200° C. The pressure in the reaction is usually in a range of 10 to 200 kg/cm$^2$ preferably 30 to 150 kg/cm$^2$. The reaction time is 0.5 to 10 hours preferably 1 to 7 hours.

The molar ratio of olefinic compound to cobalt is 10 to 1000 preferably 30 to 300. The atomic ratio of phosphorous to cobalt is 1 to 10 preferably 1 to 2. The concentration of cobalt in the reaction mixture is in a range of 0.005 to 1 wt. % preferably 0.03 to 0.3 wt. %.

The selection of the conditions for the reaction of dicyclopentadiene is especially important in the process of the present invention.

In the conventional hydroformylation of monoolefin or diolefin which are not decomposed, the variation of the condition for reaction affects only for a reaction velocity and a distribution of isomers of the products except a special condition for preventing stable action of the catalyst.

On the other hand, in the hydroformylation of dicyclopentadiene, when the condition for reaction is not suitable, an yield of the object products is low and sometimes, the reaction is stopped. This reason is not clear, however, it is considered that the reverse Diels Alder reaction of dicyclopentadiene is predominant and the resulting cyclopentadiene is selectively coordinated to the catalyst, vacant coordination sites required for the hydroformylation are lost.

In order to perform smoothly the reaction and to obtain the object product at high yield, it is necessary to select suitable conditions. Thus, the effects of the conditions for reaction are complicate and are related each others. The selection of the conditions for reaction is not simple. The conditions for reaction which highly affect to the smooth reaction among these conditions are the pressure in the reaction, the ratio of dicyclopentadiene to cobalt and the concentration of cobalt in the reaction mixture.

The pressure in the reaction is usually in a range of 50 kg/cm$^2$ to 200 kg/cm$^2$ preferably 70 kg/cm$^2$ to 150 kg/cm$^2$. The higher pressure is advantageous for the reaction.

The molar ratio of dicyclopentadiene to cobalt is usually in a range of 20 to 300 preferably 40 to 200. The lower ratio is advantageous for the reaction.

The concentration of cobalt in the reaction mixture is in a range of 0.01 to 0.5% by weight preferably 0.03 to 0.3% by weight. The higher concentration of cobalt is advantageous for the reaction.

The three conditions affect to the reaction with relations each other. The effect can be shown as a whole by a factor for oxonation F as the parameter.

$$F = \frac{\left(\begin{array}{c}\text{Co concentration in}\\ \text{reaction mixture (wt. \%)}\end{array}\right) \times \left(\begin{array}{c}\text{pressure in}\\ \text{reaction (kg/cm}^2\text{)}\end{array}\right)^{0.5}}{(\text{moles of dicyclopentadiene/gram atoms of Co})^{1.5}} \times 10^4$$

In the condition for reaction to give the factor F of higher than 5, the reaction performs smoothly to produce tricyclodecanedimethylol in the yield of higher than about 50%. Moreover, byproducts are mainly cyclopentyl carbinol and tricyclodecanemonomethylol which are effectively utilized.

When the factor F is less than 5, the reaction is stopped to give the yield of tricyclodecanedimethylol of less than about 15%. The most of the by-products are heavy materials which may be produced by condensations of the starting materials and/or the intermediates. The utilization of the heavy materials is not expected. As discussed, the feature of the reaction is remarkably different at the factor F of higher or lower than 5.

The feature of the reaction is not varied at the factor F of higher than 5, however, the selectivity of the product is different depending upon the difference of the condition for reaction.

The yield of tricyclodecanedimethylol in this region is related to the factor F and is increased depending upon the increase of the factor F. The yield is varied depending upon the kind of the phosphine and other conditions for reaction and is usually higher than about 70% at the factor F of higher than about 10.

The other conditions for reaction are selected as follows.

The reaction temperature is usually in a range of 160° to 220° C. preferably 180° to 200° C. The reaction time is usually in a range of 2 to 10 hours preferably 3 to 7 hours. The atomic ratio of phosphorus to cobalt is usually in a range of 1 to 10 preferably 1.1 to 2.

These conditions mainly affect to the reaction velocity and the stability of the catalyst, but does not substantially affect to the selectivity for the products.

If desired, the reaction can be carried out after adding a desired additive such as polymerization inhibitor and a base.

5. SEPARATION AND PURIFICATION

When a hydrocarbon is used as the solvent, the solvent can be separated from the products by cooling the reaction mixture after the hydroformylation.

The lower temperature is preferable for the separation. At the lower temperature, the viscosity of some polycyclic diol is higher whereby the handling in the processing is not easy. Thus, the separation is carried out at room temperature to 100° C. It is possible to carry out the separation under the pressures of carbon monoxide and hydrogen as those of the reaction. In usual, excess of carbon monoxide and hydrogen are removed and the separation is carried out under a pressure of from the atmospheric pressure to 10 kg/cm$^2$ in the mixed gas of carbon monoxide and hydrogen or an inert gas.

In accordance with the separation, most of the cobalt component and the phosphine are included in the solvent phase in a form of an active complex. Therefore, the solvent phase containing them can be recycled to the reaction system for hydroformylation to reuse them. If necessary, it is preferable to remove impurities which are accumulated during the recyclings.

The process of the present invention can be applied as a process for extracting the catalyst from polycyclic diol containing the catalyst of the cobalt carbonyl complex and the phosphine; with a hydrocarbon to recover the catalyst and to purify polycyclic diol.

That is, the polycyclic diol phase obtained by the above-mentioned operation includes a small amount of the catalyst. The content of the catalyst can be further decreased by extracting it with a hydrocarbon solvent. The solvent used in the extraction is preferably a saturated hydrocarbon or an aromatic hydrocarbon as those of the reaction. It is not always necessary to use the same solvent as that of the reaction. A lower boiling solvent which is easily recovered can be used. Moreover, the extraction can be carried out for two or more times. When the extraction is carried out, the extracted solvent containing the catalyst is combined to a part of the solvent for reaction and the mixture is distilled to recover the solvent for extraction and to transfer the catalyst into the solvent for reaction and the solvent containing the catalyst can be recycled into the reaction system.

This process can be also applied for a purification of polycyclic diol containing the catalyst of the cobalt carbonyl complex and the phosphine obtained by the other process.

The polycyclic diol phase is treated by a desired treatment, for example, hydrogen treatment to decompose the remaining catalyst complex, if necessary, and then, it is distilled to remove the by-products and the product of polycyclic diol can be obtained.

The present invention has been mainly illustrated as the hydroformylation of dicyclopentadiene to produce tricyclodecanedimethylol and the separation of the catalyst of the cobalt carbonyl-phosphine complex. Thus, the process can be applied for the other starting materials as the polycyclic bridged ring olefinic compound having another double bond or formyl or methylol group as described above.

The present invention will be further illustrated by certain examples which are provided for purposes of illustration only and are not intended to be limiting the present invention.

EXAMPLE 1

In a 100 ml. autoclave made of Hastelloy equipped with an electromagnetic stirrer, 6.6 g. of dicyclopentadiene, 0.197 g. of dicobalt octacarbonyl as a cobalt compound, 0.871 g. of tri-n-octylphosphine as a phosphine and 24 g. of n-dodecane as a solvent were charged and a reaction was carried out at 200° C. under a pressure of synthesis gas at a molar ratio of $CO/H_2$ of 1:1 under a pressure of 150 kg/cm$^2$ for 5 hours.

A factor for oxonation F was 95.2. After the reaction, the product was cooled and discharged at about 90° C. from the reactor and cooled to a room temperature. It was separated into a solvent phase and tricyclodecanedimethylol phase. The tricyclodecanedimethylol phase was extracted for two times with 24 g. of n-dodecane. The compounds included in the phases were analyzed, for example, organic compounds were analyzed by a gas chromatography, a cobalt was analyzed by an atomic absorption method and a phosphine was analyzed by a gas chromatography or a colorimetric method. As a result, it was found that a conversion of dicyclopentadiene (DCP) in a hydroformylation was 100%; an yield of tricyclodecanedimethylol (TCDDM) was 69.2%; an yield of tricyclodecanemonomethylol (TCDMM) was 11.7% and an yield of cyclopentyl carbinol (CPC) was 14.6%.

In a phase separation of the reaction, 92.9% TCDDM, 72.1% of TCDMM and 76.4% of CPC (based on each component) were included in TCDDM phase whereas only 8.1% of the cobalt component and 5.9% of the phosphine (based on each component) were included in TCDDM phase.

In the extracted TCDDM phase obtained by extracted by n-dodecane for one time, 86.7% of TCDDM, 43.0% of TCDMM and 46.5% of CPC (based on each component) were included whereas only 4.3% of the cobalt component and 3.5% of the phosphine were remained.

In the extracted TCDDM phase obtained by the second extraction method, 79.2% of TCDDM, 20% of TCDMM and 27.3% of CPC were included whereas only 2.8% of the cobalt component and 2.2% of the phosphine were remained.

EXAMPLE 2

In accordance with the process of Example 1 except using 0.515 g. of tri-n-butylphosphine as the phosphine, the reaction, the separation and the extraction were carried out.

The factor F in this condition was 92.5.

As a result, a conversion of DCP was 100%, an yield of TCDDM was 66.7%, an yield of TCDMM was 12.3% and an yield of CPC was 9.3%.

After the reaction, the reaction product was separated and extracted for two times and the ratios of the products and the catalyst components (based on each component) included in TCDDM phases were measured. The results are as follows.

| Operation | Separation after reaction | 1st Extraction | (unit %) 2nd Extraction |
|---|---|---|---|
| TCDDM | 93.9 | 90.4 | 79.4 |
| TCDMM | 77.4 | 54.9 | 30.4 |
| CPC | 85.0 | 58.4 | 33.3 |
| Cobalt | — | — | 5.6 |
| Phosphine | 9.1 | 3.1 | 2.5 |

EXAMPLE 3

In accordance with the process of Example 1 except using 0.401 g. of cobalt octanoate and 1.003 g. of a mixture of 9-eicosyl9-phosphabicyclo-[4.2.1]nonane and 9-eicosyl-9-phosphabicyclo[3.3.1]nonane and reacting under the pressure of 70 kg./cm$^2$, the reaction, the separation and the analyses were carried out without an extraction.

The factor F in this condition was 62.1. As a result, a conversion of DCP was 100%, an yield of TCDDM was 80.0%, an yield of TCDMM was 14.4% and an yield of CPC was 3.6%. The ratios of the products and the catalyst components (based on each component) included in the TCDDM phase were measured. The results are as follows.

| Operation | Separation after reaction |
|---|---|
| TCDDM | 83.2 |
| TCDMM | 64.4 |
| CPC | 85.3 |
| Cobalt | 7.2 |
| Phosphine | 7.8 |

EXAMPLE 4

In accordance with the process of Example 3 except using 24 g. of dodecylbenzene as the solvent and 0.198 g. of cobalt octanoate, the reaction, and the separation were carried out.

The separated TCDDM phase was extracted with 24g. of dodecylbenzene and analyzed. As a result, a conversion of DCP was 100%, an yield of TCDDM was 61.7% and an yield of CPC was 4.9%.

The ratios of the products and the catalyst components (based on each component) included in the TCDDM phase were measured. The results are as follows.

| Operation | Separation after reaction | 1st Extraction |
|---|---|---|
| TCDDM | 94.1 | 85.8 |
| TCDMM | — | — |
| CPC | 74.7 | 30.4 |
| Cobalt | 5.7 | 3.7 |
| Phosphine | 4.8 | 1.0 |

EXAMPLE 5

In accordance with the process of Example 4 except using 24 g. of decalin as the medium for the reaction and 24 g. of decalin for the extraction, the reaction, the separation, the extraction and the analyses were carried out. As a result, a conversion of DCP was 100%, an yield of TCDDM was 66.3%, an yield of TCDMM was 14.3% and an yield of CPC was 4.7%. The ratios of the products and the catalyst components (based on each component) included in the TCDDM phase were measured. The results are as follows.

| Operation | Separation after reaction | 1st Extraction |
|---|---|---|
| TCDDM | 87.8 | 80.8 |
| TCDMM | 71.9 | 31 |
| CPC | 90.4 | 51.8 |
| Cobalt | 4.5 | 3.0 |
| Phosphine | 1.5 | 0.5 |

EXAMPLE 6

In a 100 ml. autoclave made of Hastelloy C equipped with an electromagnetic stirrer, 6.6 g. of dicyclopentadiene, 0.427 g. of cobalt octanoate, 0.420 g. of a mixture of 9-eicosyl-9-phosphabicyclo[4.2.1]nonane and 9-eicosyl-9-phosphabicyclo-[3.3.1]nonane and 15 ml. of n-dodecane were charged, and a reaction was carried out with a synthesis gas at a molar ratio of $CO/H_2$ of 1:1 under a pressure of 70 kg/cm$^2$ G at 200° C. for 5 hours. The autoclave was cooled to 90° C. to separate the reaction mixture into a solvent phase and a tricyclodecanedimethylol phase. After the removal of the solvent phase, hydrogen was fed under a hydrogen pressure of 70 kg/cm$^2$ G to carry out a hydrogenation at 250° C. for 3 hours. The treated product was dissolved into 23 ml. of dioxane and then, metallic cobalt in the suspension was separated by a filtration. The wall of the autoclave was washed with 20 g. of 3% nitric acid to dissolve the cobalt component adhered on the wall. Amounts of the suspended cobalt components, and cobalt components adhered on the wall and remained in the solution were respectively measured by an atomic absorption method to give respectively 6.3%, 3.2% and 3.4% based on the charged cobalt.

A carbonyl value (mg. of CO group in 1 kg. of the product) was 6200.

When, only oxonation of this example was carried out, the carbonyl value of the product was 10,300.

EXAMPLE 7

In a 100 ml. autoclave made of Hastelloy equipped with an electromagnetic stirrer, 7.20 g. of 5-vinyl bicyclo[2.2.1]hept-2ene, 0.103 g. of dicobalt octacarbonyl as a cobalt compound, 0.646 g. of tri-n-dodecylphosphine as a phosphine and 15 ml. of n-dodecane as a solvent were charged and a reaction was carried out at 200° C. under a pressure of a synthesis gas at a molar ratio of $CO/H_2$ 1:1 under a pressure of 70 kg./cm$^2$ for 5 hours.

After the reaction, the product was cooled and discharged at about 90° C. from the reactor and cooled to a room temperature. It was separated into a solvent phase and a product phase. The compounds included in the phases were analyzed, for example, the product was analyzed by a gas chromatography, a cobalt was analyzed by an atomic absorption method and a phosphine was analyzed by a colorimetric method. As a result, an yield of the product of the corresponding diol was 53.1% and 98.1% of the product was included in the product phase. Ratios of the cobalt compound and the phosphine included in the product phase were respectively 3.8% and 6.9% based on the total cobalt component and the total phosphine.

EXAMPLE 8

In accordance with the process of Example 7 except using 0.508 g. of a mixture of 9-eicosyl-9-phosphabicyclo-[4.2.1]nonane and 9-eicosyl-9-phosphabicyclo-[3.3.1]nonane, the reaction, the separation and the analysis were carried out without an extraction.

As a result, an yield of the product of the corresponding diol was 67.2% and ratios of the product, the cobalt component and the phosphine included in the product phase were respectively 98.2%, 14.6% and 26.0% based on the total product, the total cobalt and the total phosphine.

EXAMPLES 9 AND 10

In accordance with the process of Example 8 except using each olefin shown in the following table as the starting material, the reaction, the separation and the analysis were carried out. The results are shown in the following table.

TABLE

| Example | 9 | 10 |
|---|---|---|
| Starting material olefin |  | 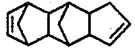 |
| Amount (g.) | 7.44 | 11.88 |
| Yield of product diol (%) | 78.2 | 75.3 |
| Ratio of each component in product phase to total of each component | | |
| Product diol (%) | 98.9 | 95.8 |
| Cobalt (%) | 9.8 | 28.6 |
| Phosphine (%) | 17.5 | 30.5 |

We claim:

1. A process for producing tricyclodecanedimethylol comprising reacting dicyclopentadiene with carbon monoxide and hydrogen in the presence of a catalyst comprising a cobalt carbonyl-phosphine complex in a suitable solvent, whereby a reaction mixture is formed, wherein the temperature, pressure, and concentration of reagents are chosen so that the F parameter defined by the following equation:

$$F = \frac{(\text{weight \% of Co in reaction mixture}) \times (\text{pressure in kg/cm}^2)^{0.5}}{(\text{moles of dicyclopentadiene present}/\text{gram atoms of Co present})^{1.5}} \times 10^4$$

is greater than 5.

2. The process of claim 1 wherein the temperature is 100°–250° C.

3. The process of claim 1 wherein the temperature is 150°–200° C.

4. The process of claim 1 wherein the pressure is 50–200 kg/cm$^2$.

5. The process of claim 1 wherein the pressure is 70–150 kg/cm$^2$.

6. The process of claim 1 wherein the concentration of cobalt in said reaction mixture is 0.005 to 1 percent by weight.

7. The process of claim 1 wherein the concentration of cobalt in said reaction mixture is 0.03 to 0.3 percent by weight.

8. The process of claim 1 wherein the molar ratio of dicyclopentadiene to cobalt is from 10 to 1000.

9. The process of claim 1 wherein the molar ratio of dicyclopentadiene to cobalt is from 30 to 300.

10. The process of claim 1 wherein the molar ratio of dicyclopentadiene to cobalt is from 40 to 200.

11. The process of claim 1 wherein the atomic ratio of phosphorus to cobalt in said complex is from 1 to 10.

12. The process of claim 1 wherein the atomic ratio of phosphorus to cobalt in said complex is from 1 to 2.

* * * * *